(12) United States Patent
Bugarin

(10) Patent No.: US 6,409,694 B1
(45) Date of Patent: Jun. 25, 2002

(54) NECK BRACE

(75) Inventor: Carlito V. Bugarin, 9547 2nd Ave. NW., Seattle, WA (US) 98117

(73) Assignee: Carlito V. Bugarin, Seattle, WA (US)

( * ) Notice: Subject to any disclaimer, the term of this patent is extended or adjusted under 35 U.S.C. 154(b) by 0 days.

(21) Appl. No.: 09/602,296

(22) Filed: Jun. 23, 2000

(51) Int. Cl.[7] ................................................. A61F 5/00
(52) U.S. Cl. ................................. 602/18; 128/DIG. 23
(58) Field of Search ............... 602/18, 17; 128/DIG. 23

(56) References Cited

U.S. PATENT DOCUMENTS

| | | | | |
|---|---|---|---|---|
| 3,224,439 A | * | 12/1965 | Blair | 602/18 |
| 3,345,983 A | * | 10/1967 | Denny | 602/18 |
| 4,338,685 A | * | 7/1982 | LaPorta | 2/2 |
| 4,543,947 A | | 10/1985 | Blackstone | 128/75 |
| 4,620,530 A | | 11/1986 | Lanier et al. | 128/75 |
| 4,702,233 A | | 10/1987 | Omicioli | 128/75 |
| 4,782,824 A | * | 11/1988 | Davies | 602/18 |
| 5,437,613 A | | 8/1995 | Reggio et al. | 602/18 |
| D368,527 S | | 4/1996 | Brooke | D24/191 |
| D379,232 S | | 5/1997 | Brooke | D24/191 |
| 5,840,051 A | | 11/1998 | Towsley | 602/19 |
| D419,267 S | | 1/2000 | Hartunian | D29/100 |
| 6,058,517 A | | 5/2000 | Hartunian | 2/468 |

* cited by examiner

*Primary Examiner*—Michael A. Brown
(74) *Attorney, Agent, or Firm*—Craig P. Wong

(57) ABSTRACT

A ventilated neck brace that provides support to the wearer's neck while providing improved ventilation and breathability. Most embodiments of the neck brace include an elongate member that defines a neck support, a transition section, and an elongate shoulder rest. Most configurations of the neck brace allow the wearer to adjust the width and length of the neck brace.

22 Claims, 7 Drawing Sheets

NECK BRACE

BACKGROUND OF THE INVENTION

The present invention relates generally to neck braces, and more specifically to neck braces which improve the air circulation and ventilation of a wearer's neck.

Neck braces or cervical collars are commonly used to support a user's neck whose muscle, cervical vertebrae, or discs have been damaged. The braces and collars substantially immobilize the wearer's head while relieving the pressure on the spine.

One conventional neck braces is a foam neck brace. Unfortunately, the foam neck braces are bulky and completely surrounds the wearer's neck. Such neck braces are difficult to ventilate and after an extended period of use, the neck of the wearer can become sweaty and irritated from the accumulated perspiration. While it is adequate functionally, during the spring and summer months it is often uncomfortable for the user to wear due to the lack of "breathability."

Accordingly, what is needed is a brace which provides adequate support to the neck while allowing air circulation and ventilation.

SUMMARY OF THE INVENTION

The present invention provides a ventilated neck brace that provides support to the wearer's neck while providing improved ventilation and breathability. Most embodiments of the neck brace are comprised of an elongate member that defines a neck support, a transition section and an elongate shoulder rest. Most configurations of the neck brace allow the wearer to adjust the width and length of the neck brace.

In a first aspect the present invention provides a neck brace having an elongate neck support section that defines an open front portion. An elongate shoulder rest supports the elongate support section. A transition section is connects the neck support to the shoulder rest. In most embodiments, the neck support section only contacts the sides and back of the wearer's neck. Such a configuration provides a supportive, low profile, lightweight, breathable, and comfortable neck brace.

In another aspect the present invention provides a neck brace having an elongate flexible member and an elongate rigid member which fits over the elongate flexible member. The elongate rigid member and elongate flexible member are shaped to form a neck support which can contact a wearer's neck and a shoulder rest which can rest over a wearer's shoulders.

In a further aspect, the present invention provides a neck brace comprising a continuous elongate member that is shaped to form a neck support, a transition section that maintains the position of the neck support, and a shoulder rest that can contact a wearer's shoulders to stabilize the neck support.

For a further understanding of the nature and advantages of the invention, reference should be made to the following description taken in conjunction with the accompanying drawings.

DESCRIPTION OF THE SPECIFIC EMBODIMENTS

Figure 1:
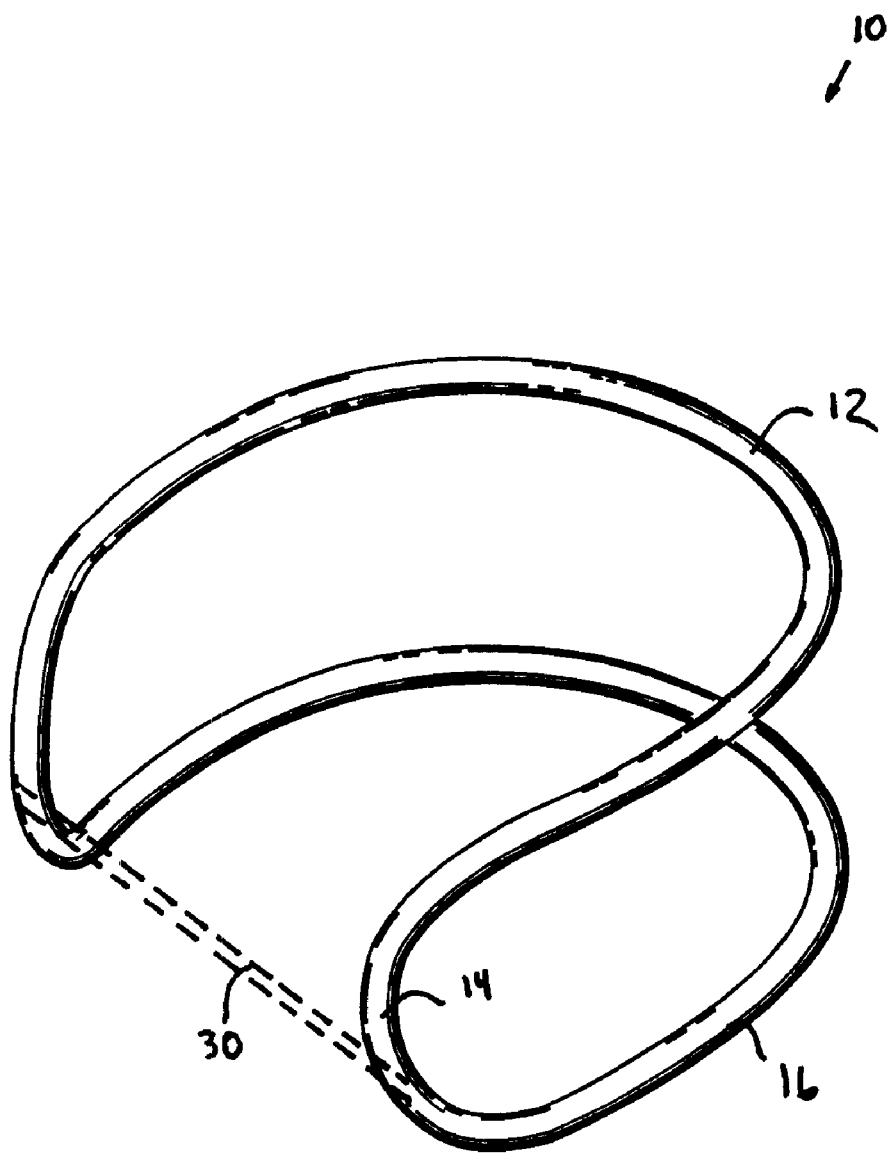
FIG. 1 is a perspective view of a neck brace incorporating the present invention.
Figure 2:
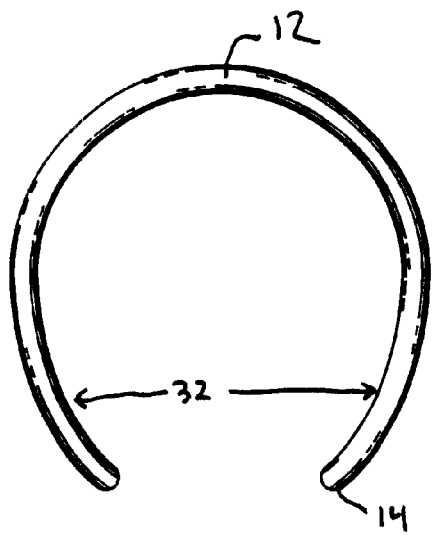
FIG. 2 is a top view of the neck brace of FIG. 1.
Figure 3:
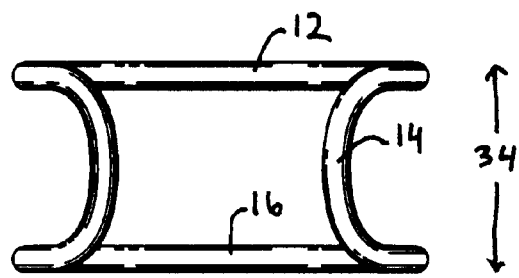
FIG. 3 is a right plan view of the neck brace of FIG. 1.
Figure 4:
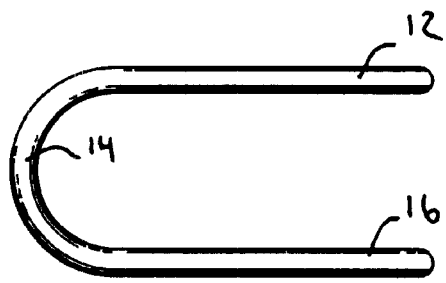
FIG. 4 is a left plan view of the neck brace of FIG. 1.
Figure 5:
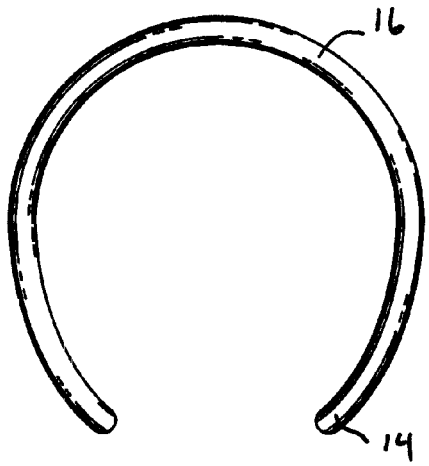
FIG. 5 is a front view of the neck brace of FIG. 1.
Figure 6:
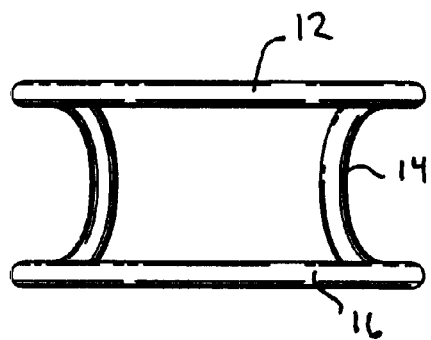
FIG. 6 is a back view of the neck brace of FIG. 1.
Figure 7:
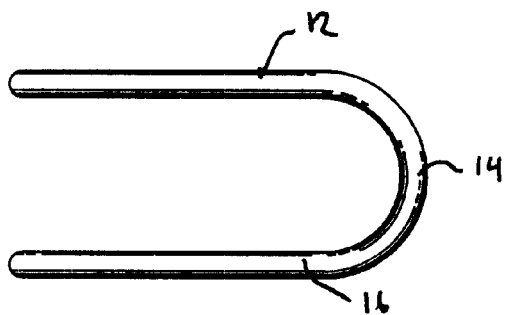
FIG. 7 is a bottom view of the neck brace of FIG. 1.
Figure 8:
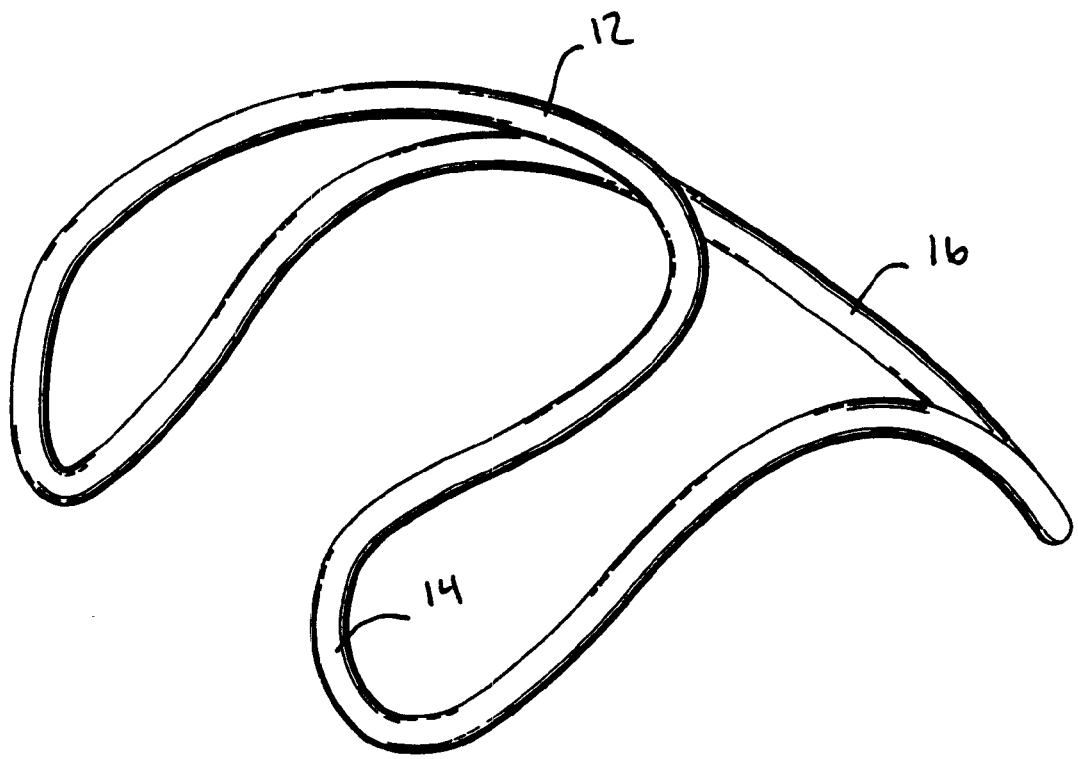
FIG. 8 is a perspective view of an alternative embodiment of a neck brace.
Figure 9:
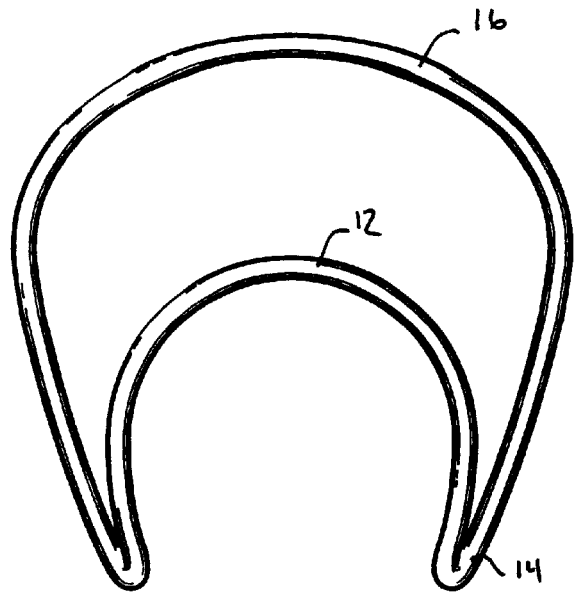
FIG. 9 is a top view of the neck brace of FIG. 8.
Figure 10:
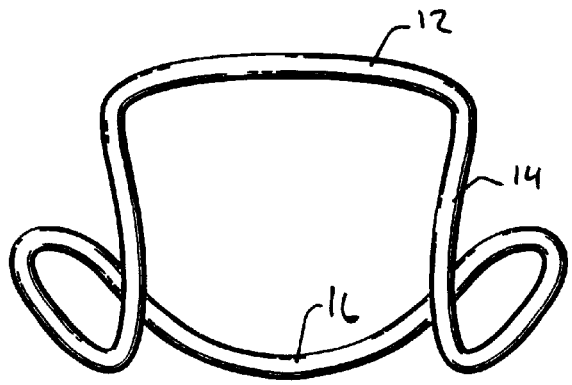
FIG. 10 is a right plan view of the neck brace of FIG. 8.
Figure 11:
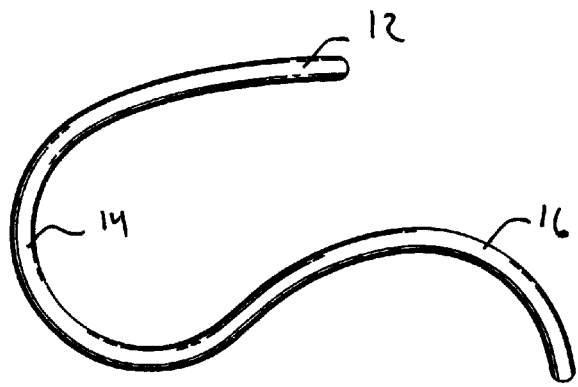
FIG. 11 is a left plan view of the neck brace of FIG. 8.
Figure 12:
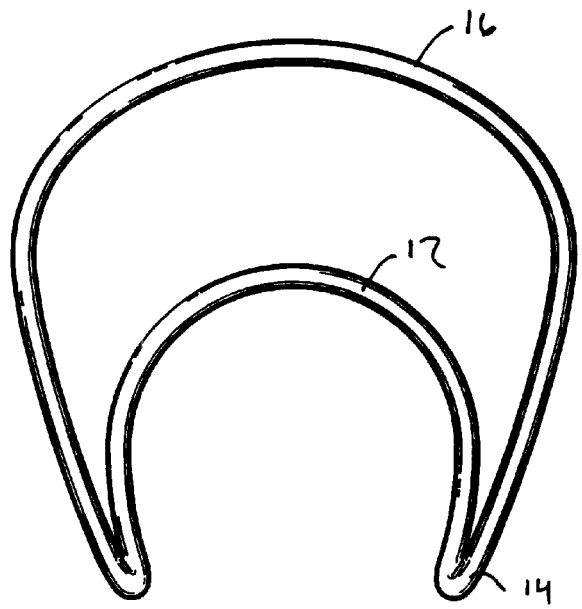
FIG. 12 is a front view of the neck brace of FIG. 8.
Figure 13:
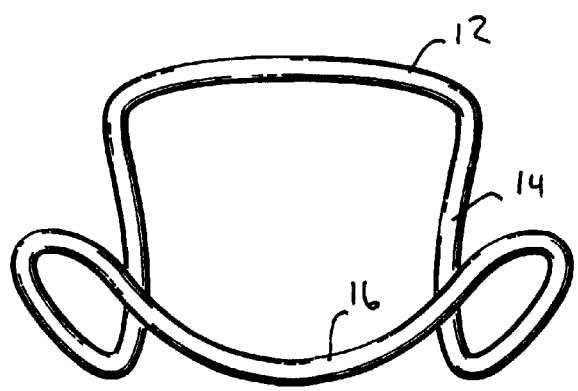
FIG. 13 is a back view of the neck brace of FIG. 8.
Figure 14:
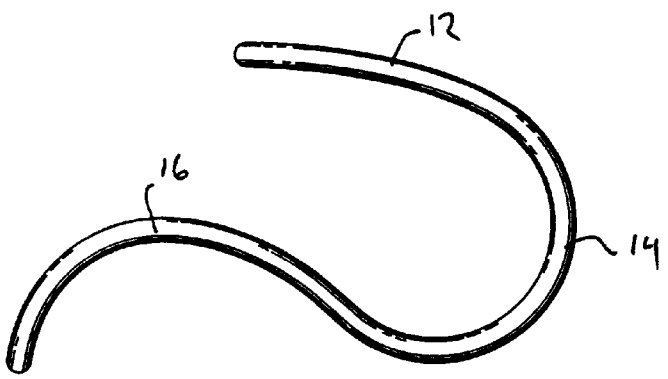
FIG. 14 is a bottom view of the neck brace of FIG. 8.

The present invention provides a low profile, adjustable neck brace that supports a wearer's neck while providing improved ventilation for the neck. The neck brace typically comprises a neck section that is coupled to a shoulder or neck rest. In some embodiments, the neck support section of the neck brace is C or U shaped so as to provide an open portion along a front area of a wearer's neck. The open portion allows the wearer to easily slip the neck brace onto the neck. Once the neck brace has been placed onto the wearer's shoulder and neck, the wearer can adjust the width and height of the neck brace, as will be described more fully below. Because of the low profile of the neck brace, the wearer can wear the neck brace under his or her clothes such that the neck brace is substantially hidden from view.

The neck brace is typically composed of an inner flexible member and an outer member that extends substantially coaxially over the inner flexible member. The inner flexible portion can be copper, aluminum, or any other material that is flexible enough to allow flexing or adjustment of the neck brace. In most embodiments, the outer member is substantially rigid so as to provide support to the inner flexible portion. By being substantially rigid, it is meant that the outer member can help prevent the inner flexible portion from being easily deformed while supporting the neck. For example, Applicant has found that when the neck brace was fabricated using only a copper tube, that the copper tube was not able to sufficiently support the wearer's neck. By covering the copper tube with a plastic sheath, the combination was able to provide sufficient support to the neck while providing improved breathability and aesthetics.

In other embodiments, where more support is needed for the neck, the material of the neck brace can be chosen to be more rigid and can be preshaped to form the neck brace shape. In such configurations, the outer member does not have to be rigid and can comprise padding, or the like. Alternatively, in other configurations, the outer member may be left off completely.

In most embodiments, the neck brace comprises a continuous elongate member. The elongate member can be shaped to define the neck support section, a transition section, and the shoulder rest section. The ends of the elongate member can be attached together with a snap fitting, tape, a weld, glue, or the like. It should be appreciated however, that the present invention is not limited to a neck brace comprised of a single, continuous elongate member. For example, the neck brace can be comprised of a plurality of materials that are attached together. Moreover, portions of the inner flexible member can be strengthened, or portions of the neck brace may be shaped so as to provide a more comfortable fit.

FIGS. 1–14 illustrates a neck brace embodying the concept of the present invention. The neck brace 10 includes an elongate neck support 12, a transition section 14, and an elongate shoulder rest 16.

Figure 15A:
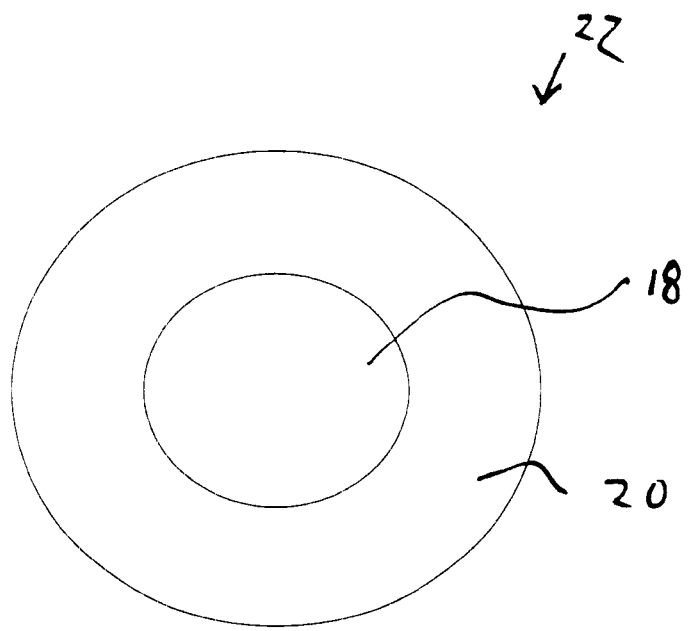
FIGS. 15A and 15B show two cross sections of the neck brace of the present invention.
Figure 15B:
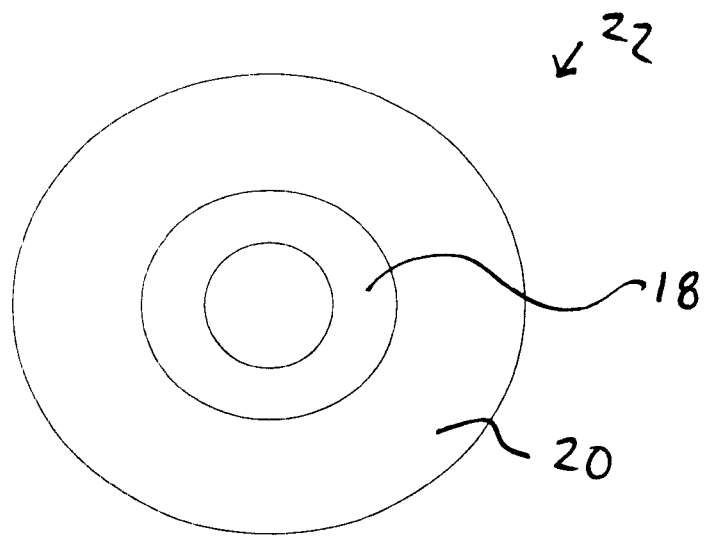

As shown by the cross section in FIGS. 15A and 15B, most embodiments of the neck brace 10 are comprised of a flexible inner member 18 and an outer support member 20. The combination 22 provides a limited amount of flexibility so as to allow the wearer to adjust the height and width of the neck brace to fit the wearer's neck, while still providing adequate support to the wearer's head and neck. In preferred embodiments, the neck support 12 is C or U shaped so as to contact the back and sides of the wearer's neck. The neck support 12 should fit snugly around the top of the neck and underneath a mandible (e.g. jaw bone) so as to limit rotation movement of the neck, lateral movement, and posterior movement of the neck. Because the neck support 12 contacts the wearer on the mandible, even though the front of the neck is not directly contacted by the neck brace 12, the forward movement of the neck is limited. In some embodiments, a forward stop 30 can be coupled to the neck support 12 or the transition section (shown in phantom in FIG. 1) to completely surround the wearer's neck and to completely prevent the user from moving the head in a forward direction.

In some embodiments, the shoulder rest 16 extends around the base of the wearer's neck (FIGS. 1–7). In other embodiments, the shoulder rest 16 can extend farther down around the wearer's shoulders so as to provide more support for the brace (FIGS. 8–14). Unlike conventional halo neck braces, a vest or body straps are not needed to couple the neck brace to the wearer's body. As shown in FIGS. 1–7, the shoulder rest 16 can extend in a C-shape around the user's back so as to provide a comfortable fit around the wearer's back and shoulders.

The transition section 14 is usually formed in a C or U shape to couple the neck support 12 to the shoulder rest 16. The transition section functions to resiliently support and maintain the position of the neck in a substantially immobilized position. The transition section 16 supports the neck support 12 so that the wearer can not move the head, anteriorly, posteriorly, or laterally.

In exemplary embodiments, the neck brace 10 is composed of a single elongate member 22 that is shaped to form the neck support 12, transition section 14 and shoulder rest 16. As described above, in most embodiments the elongate member 22 can comprise an inner flexible tubing 18 (either hollow or solid) and outer support member 20. The inner flexible member 18 provides flexibility so as to allow the neck brace 10 to be adjusted width wise 32 and height wise 34. This allows the neck brace 10 to be easily put on and adjusted for a variety of neck lengths and widths. For example, after the wearer has placed the neck brace 10 over the neck and shoulder, the wearer can spread apart or squeeze together the transition section 14 to adjust the width 32 of the neck brace to fit the user. Furthermore, to adjust the height 34 of the neck support 12, the wearer can manually spread apart or squeeze together the neck support 12 and shoulder rest 16.

In one exemplary embodiment, the neck brace 10 includes a ¼ inch hollow copper tubing 18 that is disposed within an outer plastic tubing 20. The copper tubing is shaped to form the neck support 12, the transition section 14, and the shoulder rest 16. For a 17 inch neck, the length of copper tubing 18 and plastic tubing 20 is approximately 36 inches long. The copper tubing 18 provides the neck brace 10 with the resilience and flexibility to be adjusted, while the outer plastic tubing 20 provides the mechanical support to maintain the neck in a substantially immobilized position.

The general configuration of the neck brace is typically designed to hold the wearer's head and neck to a range of movement of 0° to 15° degrees. In a specific embodiment, the neck brace 10 typically allows the head to move between 0° and 15° forward, between 0° and 7° backward, and between approximately 0° and 5° laterally. Of course, depending on the adjustment and configuration of each neck brace, the amount of support needed for the patient's neck, the range of motion can vary dramatically and the present invention is not limited by the above recited range of movements.

As will be understood by those of skill in the art, the present invention may be embodied in other specific forms without departing from the essential characteristics thereof. For example, instead of placing the support member 20 over the inner flexible member 18, it is possible to reinforce the flexible member internally. Moreover, the outer member 20 may extend only over a portion of the inner flexible member 18. Additionally, it is possible to fabricate the inner flexible member using different materials, different cross sections, or with different strengths. For example, the resilient section that couples the neck support to the shoulder rest can be reinforced, either by using a different material or by enlarging the cross section, so that the resilient section provides greater support to the neck. Other modifications include fabricating the neck support 12 with a plurality of different materials, shaping the neck support 12 to provide a more comfortable fit around the neck, or covering the neck brace 10 with a third layer, such a padding, a breathable material, or the like. Accordingly, the foregoing description is intended to be illustrative, but not limiting, of the scope of the invention which is set forth in the following claims.

What is claimed is:

1. A neck brace comprising:
    a substantially U-shaped elongate neck support section that defines an open front portion;
    a substantially U-shaped elongate shoulder rest that can support the elongate neck support section; and
    a transition section that connects the neck support section to the shoulder rest.

2. The neck brace of claim 1 wherein the neck support section only contacts the sides and back of the wearer's neck.

3. The neck brace of claim 1 wherein the neck support section and shoulder rest are comprised of a flexible continuous band of material.

4. The neck brace of claim 3 wherein the continuous band of material is covered by a rigid support.

5. The neck brace of claim 4 wherein the rigid support comprises plastic.

6. The neck brace of claim 3 wherein the continuous band of material comprises copper, stainless steel, or aluminum.

7. The neck brace of claim 1 wherein the range of movement of a wearer's neck is limited to approximately 0° to 15°.

8. The neck brace of claim 1 wherein the height and width of the elongate shoulder rest and elongate neck support are adjustable.

9. The neck brace of claim 1 wherein the elongate neck support and elongate shoulder rest provide open areas that provide ventilation to the wearer's neck.

10. The neck brace of claim 1 wherein the elongate neck support comprises a first and second end, and the elongate shoulder rest comprises a first and second end, wherein the first end of the elongate neck support is attached to the first end of the elongate shoulder rest and the second end of the elongate neck support is attached to the second end of the elongate shoulder rest.

11. A neck brace comprising an elongate flexible member and an elongate rigid member which fits over the elongate flexible member, wherein the elongate rigid member and elongate flexible member are shaped to form a substantially U-shaped neck support which can contact a wearer's neck and a substantially U-shaped shoulder rest which can rest over at least one of a wearer's base of the neck and shoulders.

12. The neck brace of claim 11 wherein at least one of the elongate flexible member and elongate rigid member is continuous.

13. The neck brace of claim 11 wherein the elongate rigid member and elongate flexible member comprise first and second ends, wherein the first and second ends are in contact with each other.

14. The neck brace of claim 11 wherein the elongate flexible member and elongate rigid member define open areas which provide ventilation to a wearer's neck.

15. A neck brace comprising an elongate flexible member and an elongate rigid member which fits over the elongate flexible member, wherein the elongate rigid member and elongate flexible member are shaped to form a neck support which can contact a wearer's neck and a shoulder rest which can rest over at least one of a wearer's base of the neck and shoulders, wherein the elongate flexible member comprises a single piece of copper and the elongate member comprises a single piece of plastic.

16. A neck brace comprising a continuous elongate member that is shaped to form a substantially U-shaped neck support that is positionable about a top portion of a user's neck, a transition section that maintains the position of the neck support, and a substantially U-shaped shoulder rest that can contact at least one of a wearer's base of the neck and shoulders to stabilize the neck support.

17. The neck brace of claim 16 wherein the neck support, transition section, and the shoulder rest comprise a flexible inner tubing and a substantially rigid outer layer.

18. The neck brace of claim 16 wherein the at least one of the neck support, the transition section, and the shoulder rest is C-shaped, wherein at least one of the transition section and neck support are positioned to contact the wearer's jaw and limit a rotation and forward movement of a wearer's head.

19. The neck brace of claim 16 wherein a height and width of the neck brace are adjustable.

20. A neck brace for substantially maintaining a position of a wearer's head and neck, the neck brace comprising:
    a substantially U-shaped elongate neck support section shaped to contact at least one of a base of the wearer's head and the top of the users neck, wherein the elongate neck support section comprises a flexible material and a rigid material; and
    an elongate base coupled to the neck support, wherein the elongate base is configured to stabilize the neck support section.

21. The neck brace of claim 20 wherein the elongate neck support contacts a wearer's mandible.

22. The neck brace of claim 20 wherein the elongate neck support comprises copper surrounded by plastic.

* * * * *